US006977068B1

(12) United States Patent
Nair et al.

(10) Patent No.: US 6,977,068 B1
(45) Date of Patent: Dec. 20, 2005

(54) METHOD FOR DETECTION OF FIBRIN CLOTS

(75) Inventors: Chenicheri H. Nair, Castle Hill (AU); Elena A. Shats, Chapman (AU); William M. Burch, Gymea Bay (AU); Rodney J. Browitt, Kaleen (AU); Timothy J. Senden, Macquarie (AU)

(73) Assignee: The Australian National University, Canberra (AU)

( * ) Notice: Subject to any disclaimer, the term of this patent is extended or adjusted under 35 U.S.C. 154(b) by 0 days.

(21) Appl. No.: 09/463,082

(22) PCT Filed: Jul. 23, 1998

(86) PCT No.: PCT/AU98/00582

§ 371 (c)(1),
(2), (4) Date: Jul. 10, 2000

(87) PCT Pub. No.: WO99/04827

PCT Pub. Date: Feb. 4, 1999

(30) Foreign Application Priority Data

Jul. 24, 1997 (AU) .................................. 97/00467

(51) Int. Cl.$^7$ ...................... A61K 51/00; A61K 49/00; A61M 36/14; A61B 5/055
(52) U.S. Cl. .................. 424/1.11; 424/1.13; 424/1.65; 424/1.81; 424/9.1; 424/9.3
(58) Field of Search ............................ 424/1.11, 1.13, 424/1.65, 1.81, 9.1, 9.3

(56) References Cited

U.S. PATENT DOCUMENTS

| 5,064,634 A | * | 11/1991 | Burch ........................ 424/1.1 |
| 5,217,705 A | * | 6/1993 | Reno et al. .................. 424/1.1 |
| 5,228,444 A | * | 7/1993 | Burch ........................ 128/654 |
| 5,330,768 A | * | 7/1994 | Park et al. .................. 424/501 |
| 5,640,705 A | * | 6/1997 | Koruga ........................ 588/16 |
| 5,952,321 A | * | 9/1999 | Doherty et al. ............. 514/210 |
| 6,110,204 A | * | 8/2000 | Lazarov et al. .......... 623/11.11 |

FOREIGN PATENT DOCUMENTS

| AU | B-48324 | 10/1989 | ............ A61B 5/08 |
| WO | 93/15768 | 8/1993 | .......... A61K 49/00 |
| WO | WO 99/04826 | 2/1999 | |

OTHER PUBLICATIONS

Bonnin et al. "Complementarity of Lung Scintigraphy and D-Dimer Test in Pulmonary Embolism". European Jn. of Nuc. Med., (Apr. 1997) 24(4), 444-7.*

Burch et al. "Technegas-a New Ventilation Agent for Lung Scanning", Nuc. Med. Commun. (1986), 7(12), 365-71.*
Senden et al. "The Physical and Chemical Nature of Technegas", Jn. of Nuc. Med. (1997) vol. 38, No. 8, pp. 1327-1333.*
The Handbook of Cosmetic Science and Technology, 1$^{st}$ Edition 1993, Elservier Advanced Technology.*
Penfold et al, "Adsorption of Nonionic Surfactants on Silica Sol Particles: The Effects of Sol Type and Concentration Surfactant Type, Concentration, and Temperature". Jm of Physical Chemistry (1996), 100(46), 18133-18137.*
Pierson, H.O. The Handbook of Carbon, Graphite, Diamond, and Fullerenes. William Andrew Publishing/Noyes, 1993.*
Chinger et al. (1987) "Haemocompatibility and biological course of carbonaceous composites for cardiovascular devices" *Biomaterials* 8:18-23.
Eriksson et al. (1997) "The initial reactions of graphite and gold with blood" *J. Biomed. Mater. Res.* 37:130-136.
Rudee et al. (1980) "The Interaction of Blood with Amorphous Carbon" Proceedings, Thirty-eighth Annual Meeting Electron Microscopy Society of America, Aug., 1980, San Francisco, CA, (ed. G.W. Bailey) pps. 584-585.
Ginsberg, J.S. et al., "Evaluation of a soluble fibrin assay in patients with a suspected deep vein thrombosis," *Thrombosis and Haemostasis* (1995) 74(3):833-836.
Nozaki, T. et al., "Production of fine aerosols labeled with various radionuclides by sublimation from a graphite boat, and their properties and tracer use," *Applied Radiation and Isotopes*, Pergamon Press Ltd., Exeter, GB, (1995) 45(3): 157-165.
Nair, H. et al., "Thrombo TraceX, a new diagnostic agent with high specificity to bind fibrin in vivo," *Blood Coagulation and Fibrinolysis* (1998) 9(7):716-717.
Supplementary European Search Report dated Jul. 7, 2004 for International Application No. EP 98934690.

* cited by examiner

*Primary Examiner*—Sreeni Padmanashan
*Assistant Examiner*—Gregory W. Mitchell
(74) *Attorney, Agent, or Firm*—Greenlee, Winner and Sullivan, P.C.

(57) ABSTRACT

A method for the detection of fibrin in a source, in particular the in vivo detection of a fibrin in a patient, the method comprising supplying to the source or patient an amount of a detectable reagent comprising a plurality of discrete particles, each of the particles comprising a plurality of layers of carbon and being capable of binding to fibrin; and detecting the presence of the particles in the source. The particles may also comprise a detectable marker encased in said plurality of layers of carbon, the presence of said marker being capable of detection in said source.

9 Claims, 12 Drawing Sheets

ARTIFICIAL CIRCUIT

IMAGING OF A CLOT IN RABBIT CAUSED BY
INTRAMUSCULAR INJECTION

AUTORADIOGRAPHY OF RABBIT LUNGS WITH PULMINARY EMBOLI.

METHOD FOR DETECTION OF FIBRIN CLOTS

CROSS-REFERENCE TO RELATED APPLICATIONS

This application is the U.S. National Stage of International Application No. PCT/AU98/00582, filed on Jul. 23, 1998, published as WO 99/04827 on Feb. 04, 1999 which claims the benefit of Australian Application No. PCT/AU97/00467, filed on Jul. 24, 1997 published as WO99/04826 on Feb. 04, 1997.

TECHNICAL FIELD

The present invention relates to a method for labelling macromolecules such as fibrin, and to methods for targeting drugs, such as antithrombotic drugs to macromolecules such as fibrin in vivo. The invention also relates to a reagent for use in such a labelling or targeting method.

BACKGROUND ART

Currently available methods of labelling macromolecules, and in particular biological macromolecules such as fibrin, may be influenced by the chemistry of the detectable marker with which the macromolecule is to be labelled. In particular, subsidiary effects resulting from the chemistry of the marker and the macromolecule being labelled may cause artifactual results. Ideally, the marker should have no influence on the macromolecule to be labelled.

It is extremely important in many applications to achieve accurate and specific labelling of macromolecules such as fibrin. For example, areas of clot detection in pathological states such as deep venous thrombosis, thrombophlebitis, and lesions in the vasculature generally require accurate and specific labelling, particularly as morbidity and mortality caused by intravenous clots is an increasingly prominent public health issue throughout the world.

Currently, there are several methods of detecting intravenous clots. For example, use is commonly made of two imaging agents which have similar capabilities for identifying such clots. These include fibrinogen labelled with $^{125}$I and a labelled 3B6 monoclonal antibody. The $^{125}$I labelled fibrinogen has, however, been found to be nonspecific and capable of giving false positive results.

"Technegas" is an agent whose original purpose was to perform high quality diagnostic imaging of airways of the lungs to facilitate the detection of blood clots. This was primarily used in conjunction with a blood flow agent for the differential diagnosis of blood clots. The agent "Technegas" consists of a plurality of discrete particles, each comprising a plurality of coating layers of carbon (varying between two and ten atoms in thickness) which completely enclose a minute crystal of $^{99m}$Tc metal. The particles are stable inert hydrophobic particles having a cross-sectional dimension of between 5 and 30 nm and a thickness of about 3 nm. The "Technegas" production process creates millions of these particles suspended in a carrier gas of argon. In this form the particles may be inhaled directly and become deposited in the alveolar spaces of the lung. From this distribution can be created three-dimensional maps of the airways by detecting the gamma ray signal generated by the decay of the Tc from the excited to the ground state ($^{99m}Tc \rightarrow {}^{99}Tc$).

The possibility of using the particles in liquid suspension as a "nanocolloid" suitable for biological and industrial applications has now been investigated. In particular, investigations have been made to find methods of extracting "Technegas" particles from argon gas directly into a physiological solution such as, for example, saline solution.

DISCLOSURE OF THE INVENTION

It has been surprisingly found that particulate entities comprising carbon, particularly those of smaller dimensions, bind to macromolecules such as fibrin(ogen) and soluble fibrin.

The present invention is therefore, based on the ability of such particulate entities comprising carbon, to bind to fibrin. To do this, in vivo, the entities comprising carbon are prepared in an aqueous injectable solution (typically an isotonic solution such as 5% glucose in water) and injected intravenously. In vitro the entities may be formulated with a suitable carrier and added to a composition containing the fibrin.

Furthermore, it has been found that these particulate entities are advantageously able to enclose a detectable marker. This effectively quarantines the marker from its surrounding environment. Thus, the invention advantageously provides an effective means for labelling fibrin in vivo or in vitro.

According to one aspect of the invention there is provided a method for the in vivo detection of fibrin in a patient, the method comprising:

administering to the patient an effective amount of a detectable reagent comprising a plurality of discrete particles dispersed in a veterinarily or pharmaceutically acceptable carrier, diluent, excipient and/or adjuvant each of the particles comprising a detectable marker encased in a plurality of layers of carbon and being capable of binding to fibrin; and detecting the presence of the detectable marker in the patient.

According to another aspect of the invention there is provided a method for the detection of fibrin in a source, the method comprising:

supplying to the source a detectable reagent comprising a plurality of discrete particles dispersed in a carrier, diluent, excipient and/or adjuvant, each of the particles comprising a detectable marker encased in a plurality of layers of carbon and being capable of binding to fibrin; and detecting the presence of the detectable marker in the source.

According to a further aspect of the invention there is provided a detectable reagent for use in the in vivo or in vitro detection of fibrin, the detectable reagent comprising a plurality of discrete particles dispersed in a carrier, diluent, excipient and/or adjuvant, each of the particles comprising a detectable marker encased in a plurality of layers of carbon and being capable of binding to fibrin.

The particles are distinguished from the standard "Fullerene" derivate particles in that they comprise a plurality of layers of carbon. Also, their method of formation is different. Fullerenes are predominantly produced by a carbon arc process at low pressure, and the residue from the reaction is chemically and physically sorted into separate components for analysis or further processing. The subject discrete particles are preferably formed by a resistive or otherwise controlled thermal graphite heating process. The co-condensation reaction in which the particles are formed in this case seems to occur in the boundary region of a stable thermal plasma that has been termed a "thermo-pause". Time, temperature and pressure conditions for the "thermo-pause" determine the size of the native metal crystal and the number of graphite layers which surround it.

In a preferred embodiment, the particles are hydrophilic. In particular, it is preferred that an outer layer at least of the plurality of layers is chemically modified to permit a stable chemical association of the outer layer with an aqueous medium or solution. More particularly, the outer layer preferably comprises hydrolysed graphite. Further, to ensure that the chemistry of the detectable marker is not manifested in the environment outside of the particles, the detectable marker is preferably encased in from about 2 to 20 layers of graphitic carbon, more preferably about 2 to 10 layers of graphitic carbon.

Suitably, the reagent is administered to a patient in the form of an injectable composition containing a suitable carrier, for example 5% glucose in water. This carrier is preferred as it is non ionic and is generally accepted as a standard isotonic solution. The total mass of the particles in one dose will generally be in the order of 100 ng or less.

The detectable marker may be detected by radiometric techniques using a radionuclide, by magnetic resonance imaging, or may be optically detectable. The detectable marker may be pharmaceutically or veterinarily acceptable or otherwise (e.g. laboratory or analytically acceptable) depending on the intended use of the reagent.

Generally, radionuclides which are traditionally used in nuclear medicine including imaging techniques are suitable for use in this invention, and include radionuclides which emit gamma rays. Examples of suitable radionuclides are $^{111}$In with a half-life of 2.8 days, $^{67}$Ga, $^{68}$Ga, $^{99m}$Tc. A preferred radionuclide is $^{99m}$Tc.

An example of a detectable marker suitable for use in magnetic resonance imaging techniques is Gd.

Examples of markers detectable by optical techniques are colloidal compounds which exhibit a distinctive colour. An example is colloidal gold.

As discussed above, the particles used in accordance with the various aspects of the present invention differ from standard "Fullerene" derivative particles by both chemistry and means of production. Accordingly, the invention also provides a method of forming a detectable reagent for use in labelling fibrin, the method comprising the steps of:

heating a carbon crucible having deposited thereon a solid form detectable marker in a sealed container to a temperature of from 2250° C. to 3000° C. to form particles comprising a detectable marker encased in a plurality of layers of carbon and being capable of binding to fibrin; and precipitating the particles to form the detectable reagent.

The detectable marker may be deposited on the crucible in the solid form. Alternatively, a liquid solution of a detectable marker may be deposited onto the carbon crucible and evaporated so as to form solid residue of the detectable marker.

Where the detectable marker is $^{99m}$Tc, a liquid solution of technetium is generally used in the form of a liquid solution of sodium pertechnetate. Similarly, where the detectable label is $^{99m}$Tc, the solid form of technetium is generally sodium pertechnetate.

Preferably, the crucible is heated to a temperature in the range 2250–2900° C. more preferably 2470–2900° C., more preferably about 2600° C. to about 2700° C. In a preferred embodiment the crucible is pulse heated at from 0.1–5 secs, more preferably 1–3 seconds, more preferably 2.7 secs. It has been found that such pulse heating advantageously facilitates the production of smaller particles having a more tightly controllable size distribution.

Preferably the carbon crucible is a graphite crucible, more preferably a pure graphite crucible. The graphite may be, for example, pyrolitic graphite or porous standard graphite. However, pyrolitic graphite is preferred.

Generally the graphite crucible is heated in the presence of a substantially pure inert gas atmosphere within the sealed container. Preferably the inert gas is argon.

Suitable methods for preparing detectable markers such as radionuclides, encapsulated in a carbon are generally described in Australian Patent No. 589 578 (incorporated herein by cross reference). However, unlike heating the graphite crucible containing sodium pertechnetate to any temperature above at least 1900 or 2200° C. under an inert atmosphere so as to produce Technegas as described in Australian Patent No. 589 578 it is important to only heat the graphite crucible to a temperature in the range 2250–3000° C., more preferably 2475–2950° C., more preferably 2470–2900° C., and even more preferably about 2600° C. to about 2700° C. Generally pulse heating (0.5–3 secs) is used.

The particles may be precipitated using an electrostatic precipitator of the type described in AU 31778/95 sealed under Australian Patent No. 686861 on 25 May, 1998 (incorporated herein by cross reference), for example, and the resultant precipitate then formulated with a desired carrier or adjuvant, for example at a desired concentration dependent on the end use.

The electrostatic precipitator may include a housing defining a duct through which a gas containing carbon particles passes, the duct having an inlet and an outlet; an ion source past which the gas passes to charge the particles; an electrode between the inlet and the outlet and spaced downstream from the ion source; means to establish an electric potential between the ion source and the electrode; and wherein the electrode is coated with a soluble material to which the particles are attracted so as to become deposited thereon. An electrode for the electrostatic precipitator, may include a coating of a soluble material upon which the particles are deposited by being attracted thereto. An alternative electrostatic precipitator to collect particles from a gas stream, may include a duct through which the gas passes between an inlet and an outlet; an ion source between the inlet and the outlet past which the gas passes to have the particles charged; a reservoir containing a liquid past which the gas passes; and means to establish an electric potential between the ion source and the reservoir so that particles are attracted to the liquid. Another alternative electrostatic precipitator, includes a housing defining a duct through which a gas containing carbon particles passes, the duct having an inlet and an outlet; an ion source projecting into the duct and located between the inlet and the outlet; a wall surrounding at least part of the duct between the inlet and the outlet; means in the duct to receive a liquid; means to enable the establishment of an electric potential between the ion source and the liquid; means to cause the liquid to produce droplets to be dispersed in the duct; and wherein upon the application of the electric potential, the droplets and particles are attracted to the wall. A method of collecting particles may include the steps of passing a gas stream containing the particles, through a chamber, the gas stream including an inert gas and air; passing the gas stream past an ion source within the chamber to charge the particles; and attracting the particles to an electrode by establishing an electrical potential between the ion source and the electrode. The particles may then be removed from the electrode and formulated as required.

It has been found that addition of a trace of surfactant coating to the particles may enhance their binding efficiency by up to 10 times. Preferably, the surfactant is, for example, $C_{16}EO_6$. The concentration of the surfactant is preferably between 0.001% and 0.010% v/v, more preferably 0.003% and 0.006% v/v.

It has also been found that particles comprising a plurality of layers of carbon by themselves, i.e. particles which do not include via encapsulation a detectable marker, may also bind to fibrin.

Thus, the invention also provides methods for the detection of fibrin and reagents for the detection of fibrin as hereinbefore described, but which do not encase a detectable marker. In these cases, the detection of the particles to determine the presence or otherwise of fibrin, such as in the form of a fibrin clot, must be conducted by suitable means other than the abovementioned detection of the detectable marker.

According to certain embodiments of this invention wherein fibrin is detected in vitro, techniques such as dip-stick methods, test strip methods, ELISA methods, agglutination tests using latex suspensions, and the like may be suitably employed. These methods may make use of antibodies bound to the particles for example. Alternatively, in the case of latex, dip-stick methods and test strip methods antifibrin may be attached to the latex, dip stick or test strip (or other suitable substrate e.g. beads such as glass beads). Thus when such a latex particle, dip stick or test strip is dipped into or placed in contact with a source containing a fibrin: particle complex, it will bind the fibrin portion of the complex (as well as any free fibrin or other fibrin complexes in the composition). The latex particle, dip stick or test strip is then typically washed so as to remove any unattached components of the composition and whether and/or the amount of complex attached to the latex particle, dip stick- or test strip determined by detecting-whether the detectable label is present (and, if so, the amount present if required) on the latex particle, dip stick or test strip.

The methods of the invention are not restricted to human patients. Animal experiments have proven that this binding to fibrin occurs in deposits in deep vein thrombosis, pulmonary embolism and tumours including mammary tumours. It is envisaged that the methods of the invention may also be applicable to malignant disease such as skin cancer. The methods of the invention may be practised on mammals including a bovine, human, ovine, equine, caprine, leporine, feline or canine vertebrate. Most often, however, the methods will be practised on a human patient. In this case, the composition is a pharmaceutical composition and the carrier, diluent, excipient and/or adjuvant is pharmaceutically acceptable. Where the mammal is not human, the composition would be typically a veterinary composition and the carrier, diluent, excipient and/or adjuvant would be veterinarily acceptable. However, the methods of detection of fibrin in a source may be performed either in vivo or in vitro, including a reaction in a suitable laboratory apparatus such as a test tube or beaker followed by separation of any complex formed and detection for the presence of complex.

In this specification and claims the expression "encased" refers to total enclosure or encapsulation of the detectable marker by the carbon layers. This phenomenon may be the result of co-condensation. That is, detectable marker crystals, liquid droplets or amorphous deposits first form and then carbon is condensed around the marker to form a discrete particle. Where a marker is not required, carbon is simply prepared so as to form a particle comprising a plurality of layers of carbon.

For parenteral administration, the reagent of certain embodiments of the invention may be prepared in sterile aqueous or oleaginous solution or suspension. Suitable non-toxic parenterally acceptable diluents or solvents include water, Ringer's solution, 5% glucose in water, buffered sodium or ammonium acetate solution, 1,3-butanediol, ethanol, propylene glycol or polyethylene glycols in mixtures with water. Aqueous solutions or suspensions may further comprise one or more buffering agents. Suitable buffering agents include sodium acetate, sodium citrate, sodium borate or sodium tartrate, for example. Aqueous solutions for parenteral administration may also be suitable for administration orally or by inhalation.

The dosage form of the reagent composition will comprise typically from 0.001% to 10% by weight of the reagent. Preferably, dosage forms according to the invention will comprise from 0.1% to about 5% by weight of the reagent.

The reagent of various aspects of the invention may be prepared by means known in the art for the preparation of compositions, such as in the art of preparing veterinary and pharmaceutical compositions, including blending, grinding, homogenising, suspending, dissolving, emulsifying, dispersing and mixing of the reagent of the first embodiment together with the appropriate excipient(s), carrier(s), adjuvant(s) and/or diluent(s).

In the in vivo methods of the invention, the reagent may be administered orally or parenterally, e.g. by injection and by intra-arterial infusion, intravenously, rectally or by inhalation spray. A suitable method may comprise the administration of a single dose or multiple doses. If the application of more than one type of reagent is desired (e.g. there may be multiple reagents with different detectable markers) the reagents may be administered at the same time or at different times (including sequentially).

The administered dosage of the reagent(s) can vary and depends on several factors, such as the condition, age and size of the patient as well as the conditions under which the method is being performed. Dosages of reagent are preferable such that about 100 ng or less of the discrete particles, in terms of the total mass of all of the particles, is administered.

For oral administration, a pharmaceutical or veterinary composition comprising the reagent may be in the form of tablets, lozenges, pills, troches, capsules, elixirs, powders, including lyophilised powders, solutions, granules, suspensions, emulsions, syrups and tinctures. Slow-release, or delayed-release forms may also be prepared, for example in the form of coated particles, multi-layer tablets or microgranules.

An inhalation spray comprising the reagent(s) may be in the form of a solution, suspension or emulsion as exemplified above. The inhalation spray may further comprise an inhalable propellant of low toxicity. Suitable propellants may include for example carbon dioxide or nitrous oxide.

Illustrative of typically used pharmaceutically or veterinarily acceptable carriers or diluents are demineralized or distilled water; isotonic glucose solution. Typically, the carrier or carriers will form from 90% to 99.9% by weight of the composition.

Suitable buffering agents include salts of boric, acetic, phosphoric, citric, malic, succinic acids and the like, for example sodium citrate, sodium bicarbonate, sodium acetate and sodium phosphate. Additionally or alternatively, the free acids may be used, together with an alkali such as sodium hydroxide, sodium carbonate, sodium bicarbonate, potassium hydroxide, potassium carbonate or potassium bicarbonate. Typically, the buffering agent or agents will form from 0.1% to 20% by weight of the composition.

The following expressions are used in the Examples.

a) FullerTag: (Registered Trademark) A nanocolloid suspension (in saline or distilled water) of particles comprising 2–10 atomic layers of carbon encasing technetium crystal such that it forms a stable inert hydrophobic or hydrophilic particle whose overall dimension is between about 5 and about 30 nm in cross-section and about 3 nm in thickness.
b) ThromboTrace: FullerTag with surfactant. In the Examples, the surfactant is $C_{16}EO_6$.

The specific affinity of the multi-layered carbon particles for fibrin, whether containing or not containing a detectable marker, suggests that the invention may also be relevant to systems for "site-specific" drug delivery. In particular, it is envisaged that the affinity of the particles of the invention to fibrin may be useful in targeting, for example, antithrombotic or anti-cancer drugs to fibrin sites in order to provide more direct and effective treatment.

Accordingly, the invention also provides a method of targeting a drug to a fibrin site in vivo, the method comprising administering to a patient an effective amount of a reagent comprising a plurality of discrete particles dispersed in a veterinarily or pharmaceutically acceptable carrier, diluent, excipient and/or adjuvant, each of said particles comprising a plurality of layers of carbon and being capable of binding to fibrin, and at least some of said particles having coupled thereto a drug to be targeted to the fibrin site.

Accordingly there is also provided a method of treatment of a fibrin related disease comprising administering to a patient an effective amount of a reagent comprising a plurality of discrete particles dispersed in a veterinarily or pharmaceutically acceptable carrier, diluent, excipient and/or adjuvant, each of said particles comprising a plurality of layers of carbon and being capable of binding to fibrin, and at least some of said particles having coupled thereto a drug to be targeted to the fibrin site.

As mentioned above, the drug to be targeted may include any drug, for example anti-thrombotic or anti-cancer drugs. Furthermore, these drugs may be coupled to the particles by any suitable means including coupling methods known in the art. The particles may also encase a detectable marker as previously described. In this instance, the particles may not only target the coupled drugs to a fibrin site, but may also be used to detect the location of the fibrin site in vivo.

Following from this, the invention also provides a reagent for use in targeting a drug to a fibrin site in vivo, the reagent comprising a plurality of discrete particles dispersed in a pharmaceutically or veterinarily acceptable carrier, diluent, excipient and/or adjuvant, each of the particles comprising a plurality of layers of carbon and being capable of binding to fibrin, wherein at least some of the particles have coupled thereto a drug to be targeted to the fibrin site.

BRIEF DESCRIPTION OF THE DRAWINGS

Embodiments of the invention will now be described in more detail with reference to the accompanying drawings in which.

BEST MODES AND OTHER MODES FOR CARRYING THE INVENTION

Figure 1:
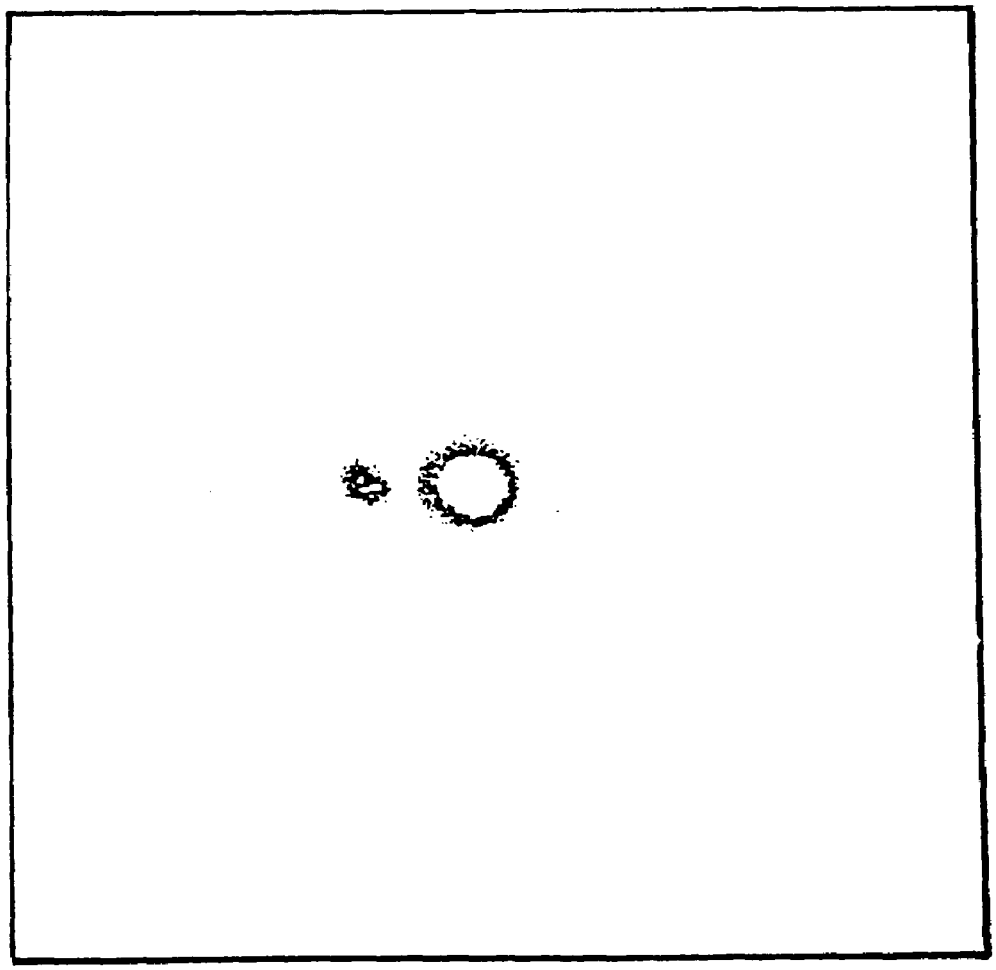
FIG. 1 is an autoradiograph of a fibrin clot in accordance with Example 12.

It is envisaged that the specific binding of particles according to the invention may be useful for:
a) imaging of clots in blood vessels in patients with deep vein thrombosis (DVT), patients with atheromatous occlusions in the vasculature and embolisms;
b) the development of target specific drugs for the dissolution of blood clots;
c) the use of technology to develop a bedside measurement of fibrin(ogen) and soluble fibrin;
d) the detection of early tumours; and
e) research tools to study clots and diseases like atherosclerosis, Deep Vein Thrombosis and any other fibrin related disease.

The mechanism for formation of the carbon particles depends on a co-condensation of the native metal crystals with the $C_3$ gas that is present above carbon at high temperatures. The reaction is carried out in an inert gas atmosphere, typically argon. Thus, the final size of the nano-encapsulates can be modified by varying the rate and duration of the heating cycle. At present, repeat short pulses of heat for 2.7 sec to temperatures as high as from 2600° C. to 2700° C. will produce particles that go to the lower limit of resolution of electron microscopes, namely 5 nm. Pyrolytic or glassy-carbon provides a better yield of activity of Tc from the crucible than the more porous standard graphite. This appears to be due to the non-absorption of the ions into the graphite matrix. Four lots of 2.7 sec heating pulses to from 2600° C. to 2700° C. in pyrolytic or glassy-carbon gives rise to a much smaller spectrum of particle size distribution than the original heating cycle of 2500° C. for 15 sec. The particles were precipitated on an electrode using a precipitator as described in Australian Patent Application No. 31778/95, sealed under Australian Patent No. 686861 on 25 May, 1998 and formulated in saline. The reagent composition may be then injected into a patient and detected in vivo so as to locate fibrin deposits.

Typically the starting material is Tc—99m as standard sodium pertechnetate for injection. The Micro-Aerosol Generator (MAGen—USA name), or particle generator is essentially a miniature high temperature furnace in which the heating element is also the source of graphite and/or carbon vapour which ultimately coats the Technetium metal. The heating element is made from 100% pure spectroscopic graphite whose electrical and mechanical specifications match the requirements of the machine. It is a 6 mm square section rod 50 mm long, machined to form a crucible in the centre section such that it can hold a liquid volume of 0.14 mL. This hollowed and thinned section also provides the high resistive portion of the rod which becomes the hottest section when electric current is passed through it. The rod is held under spring tension between two high current electrodes. The entire assembly is mounted as a drawer section sliding into the lower chamber of a 6 L vessel, and electrically powered from an automatic process-controller. The crucible is first filled with liquid Sodium Pertechnetate in normal physiological saline, which in most instances contains enough activity [260–370 MBq or 7–10 mCi] for a single patient administration. The drawer section is then closed and the automatic process takes over, gently blowing pure argon gas over the top of the crucible while warming it to 70° C. This is known as the "simmer" cycle, and takes 6 minutes, during which time the liquid in the crucible dries out and the whole chamber is purged with pure argon, replacing all the original air and water vapour. A process controller alerts the user that the machine is ready to produce the particles. At the conclusion of this preparation phase, the machine is activated via the control panel "start" button, and the crucible temperature rises to 2550° C. by resistively heating it with about 2.5 kW of power within 0.75 s (four lots of 2.7 sec heating pulses to 2700° C. in pyrolytic carbon gives rise to a much smaller spectrum of particle size distribution than the original heating cycle of 2550° C. for 15 sec) and holds that value within 50° C. for 15 s through a feedback servo from an optical sensor before switching off. This fills the 6 L chamber with gas comprising the particles which encapsulate Tc—99m. The particles are collected by passing the gas stream containing the particles, through a chamber, the gas stream including an inert gas and air; passing the gas stream past an ion source within the chamber to charge the particles; attracting the particles to an electrode by establishing an electrical potential between the ion source and the electrode. The particles are then removed from the electrode and formulated with a carrier as required.

The present invention will now be described with reference to the following examples which should not be construed as limiting on the scope thereof.

EXAMPLE 1

Particles were prepared in accordance with the methods of Australian Patent No. 589 578 except the graphite crucible was subjected to four lots of 2.7 sec heating pulses to 2700° C. in pyrolytic or glassy-carbon. The disclosure of Australian Patent No. 589 578 is hereby incorporated by reference.

EXAMPLE 2

Particles were formulated into normal saline by precipitating the particles formed as per Example 1 using precipitation apparatus and methods of Australian Patent No. 686861 the disclosure of which is hereby incorporated by reference, and then mixing the desired amount of the particles with normal saline.

EXAMPLE 3

Plasma was mixed with a small aliquot of particles formulated into saline in accordance with Example 2 and clotted with 1 U/mL thrombin. After incubation at room temperature for 1 hour the plasma clot was crushed using a wooden spatula. A gamma counter was used to count radioactivity. Radioactivity was confined to the fibrin with less than 3% of the original activity resident in the exudate.

EXAMPLE 4

A similar experiment using purified fibrinogen was performed to exclude binding to other plasma proteins. Again it was shown that only about 3% of the radioactivity was resident in the exudate.

Both these experiments show that these particles have specific binding capacity for fibrin.

EXAMPLE 5

To ensure that such labelling could not be transferred or leached from clots to whole blood or plasma, plasma clots were incubated in whole blood or plasma at 37° C. for 3 hours. The radioactivity was confined to the clot with very little escaping to the surrounding blood or plasma (0.7% radioactivity in blood and plasma, respectively).

EXAMPLE 6

Unlabelled plasma clots and clots developed from purified fibrinogen solution in glass tubes respectively were gently permeated with particles formulated into saline in accordance with Example 2. The initial washout of serum was devoid of radioactivity as expected. Further measurement showed that most of the particles were specifically bound to fibrin. These clots were removed from the glass tubes and crushed and carefully washed three times in saline and counted in a gamma-counter. Radioactivity was confined to the clot and barely detectable in the exudate.

EXAMPLE 7

Tests of the efficacy of the fibrin label were performed in vivo, using the rabbit, which is the standard model for vascular research. This experiment was performed on multiple occasions on different animals. One ear was given a small needle stick injury and particles formulated into saline in accordance with Example 2 in 1 mL volume was injected in the other ear. The rabbit was anaesthetised for the whole procedure and laid on the detector surface of a gamma camera (in this instance a GE model 400T). In the second animal there was a further small vascular injury and bruise in the ear on the side of the injection.

The injury on the ear opposite to the injection site showed an increased uptake on the "first pass" of the blood flow through the body. In the second rabbit, the injury proximal to the injection site labelled much more strongly than that in the other ear, but then washed out over a period of twenty minutes. Dynamic analysis showed that the initial uptake and the washout followed by a renewed uptake slowly with time, occurred in both animals at about the same rate.

Examples 8–16 and 22–25 relate to in vitro studies while Examples 17–21 relate to in vivo studies.

EXAMPLE 8

Binding of ThromboTrace to Fibrin

Protocol: Fibrin network developed from 1 mL pooled human plasma obtained from healthy donors (by adding 1 U/mL bovine thrombin (Parke Davis) and 25 mMCaCl$_2$ (final concentration)) was incubated with normal saline (NS) (4 mL) containing ThromboTrace (TT) (100 µL) at 37° C. for 2 hours using an elliptical rotator. A mixture of normal saline and ThromboTrace without clot was used as control. Clots were then crushed with a wooden spatulum and counted using a gamma counter. Nanocolloid preparation of $^{99}$Tc—Sb$_2$S$_3$ (antimony sulphide) used for bone imaging was studied as a control.

Results:

| | | | |
|---|---|---|---|
| 50 µl NS + TT (initial count) | 99500 cpm | 50 µl NS + $^{99}$Tc—Sb$_2$S$_3$ (initial count) | 397800 cpm |
| 50 µL 1 NS + TT (post-incubation) | 87450 cpm | 50 µl NS + $^{99}$Tc—Sb$_2$S$_3$ (post-incubation) | 415000 cpm |
| 50 µl NS + TT + clot (post incubation) | 72870 cpm | 50 µl NS + $^{99}$Tc—Sb$_2$S$_3$ + clot (post-incubation) | 408700 cpm |
| Crushed clot on spatulum | 478720 cpm | Crushed clot on spatulum | 9430 cpm |
| After extensive wash in NS | 457436 cpm | after 3 washes in NS | 7790 |
| | | after 6 washes in NS | 3150 |

Conclusion: There is a significant decrease of the label (17%) in the incubation medium with ThromboTrace which accounts for the high count observed in the crushed fibrin clot. There is no significant changes in the activity of incubation medium with nanocolloid and there was no significant binding of $^{99}$Tc—Sb$_2$S$_3$ to fibrin, after 6 washes most of the activity washes away. This observation suggests a high specificity of ThromboTrace for fibrin.

EXAMPLE 9

Investigation of the Strength of ThromboTrace Binding to Fibrin

Protocol: ThromboTrace (TT) (50 µl) was added to pooled plasma obtained from the blood of healthy donors (5 mL). Fibrin networks were developed from 1 mL of this labelled plasma (by adding 1 U/mL bovine thrombin (Parke Davis) and 25 mMCaCl$_2$ (final concentration)) and allowed to incubate at 37° C. for 30 min. Clots were then crushed with wooden spatulum, extensively washed with normal saline and counted using a gamma counter. Nanocolloid preparation of $^{99}$Tc—Sb$_2$S$_3$ (antimony sulphide) used for bone imaging was studied as a control.

Results:

| | | | |
|---|---|---|---|
| 50 µl plasma + TT (initial count) | 58700 cpm | 50 µl plasma + $^{99}$Tc—Sb$_2$S$_3$ (initial count) | 100195 cpm |
| 50 µl expelled serum (after clot crushed) | 1600 cpm | 50 µl expelled serum (after clot crushed) | 100500 cpm |
| Crushed clot on spatulum | 1026700 cpm | Crushed clot on spatulum | 3650 cpm |
| Crushed clot on spatulum after extensive wash in normal saline | 1005850 cpm | Crushed clot on spatulum after extensive wash in normal saline | 1800 cpm |

Conclusion: Fibrin clot retained 97% of the initial radioactivity of TT solution which was tightly bound. There was no binding of nanocolloid $^{99}$Tc—Sb$_2$S$_3$ to fibrin.

EXAMPLE 10

Study of the Washout of ThromboTrace from Clot

Protocol: ThromboTrace (TT) (50 µl) was added to pooled plasma obtained from the blood of healthy donors (5 mL). Fibrin networks were developed from 1 mL of this labelled plasma (by adding 1 U/mL bovine thrombin (Parke Davis) and 25 mMCaCl$_2$ (final concentration)) and allowed to incubate at 37° C. for 30 min. The clots were incubated 37° C. for 3 hours using an elliptical rotator with 3 mL unlabelled whole blood or 3 mL unlabelled plasma. The radioactivity of incubation media was measured using a gamma counter.

Results

| | |
|---|---|
| 50 µl plasma + TT (initial count) | 58700 cpm |
| 50 µl blood incubated with labelled clot | 380 cpm |
| 50 µl plasma incubated with labelled clot | 450 cpm |
| Crushed clot on spatulum | 1026700 cpm |

Conclusion: ThromboTrace was tightly bound to fibrin, washout of label into surrounding blood or plasma was less than 1%.

EXAMPLE 11

Study of the Binding of ThromboTrace to Fibrin Under Perfusion

Protocol: Fibrin network was developed in pre-etched glass tube from 1 mL purified fibrinogen solution (2.5 mg/mL) by adding 1 U/mL bovine thrombin (Parke Davis) and 25 mMCaCl$_2$ (final concentration). The network was gently perfused with 1.5 mL normal saline containing ThromboTrace (Ti) (50 µl). The radioactivity of expelled perfusate was measured using gamma counter. Clots were then crushed with a wooden spatulum washed in normal saline and counted using a gamma counter.

Results:

| | |
|---|---|
| 50µ NS + TT (initial count) | 47500 cpm |
| 50 µl expelled perfusate | 3200 cpm |
| Crushed clot on spatulum washed with NS | 991200 cpm |

Conclusion: After the perfusion of normal saline containing ThromboTrace through fibrin network only 7% of initial radioactivity was detected in the perfusate while crushed clot retained considerable radioactivity. This observation indicates a high affinity of ThromboTrace to purified fibrin. This experiment was repeated with plasma clots and similar results were observed.

EXAMPLE 12

Study of the Specific Binding of ThromboTrace to Fibrin by Autoradiography

Protocol: Fibrin network was developed in pre-etched glass tube from 1 mL purified fibrinogen solution (2.5 mg/mL) by adding 1 U/mL bovine thrombin (Parke Davis) and 25 mMCaCl$_2$ (final concentration). The network was gently perfused with 1.5 mL normal saline containing ThromboTrace (TT) (50 µl). The tube was autoradiographed with a gamma camera (FIG. 1).

Conclusion: Clots layered with ThromboTrace and autoradiographed with a gamma camera revealed extensive binding of material within the first cm of perfusion of the clot.

EXAMPLE 13

Figure 2:
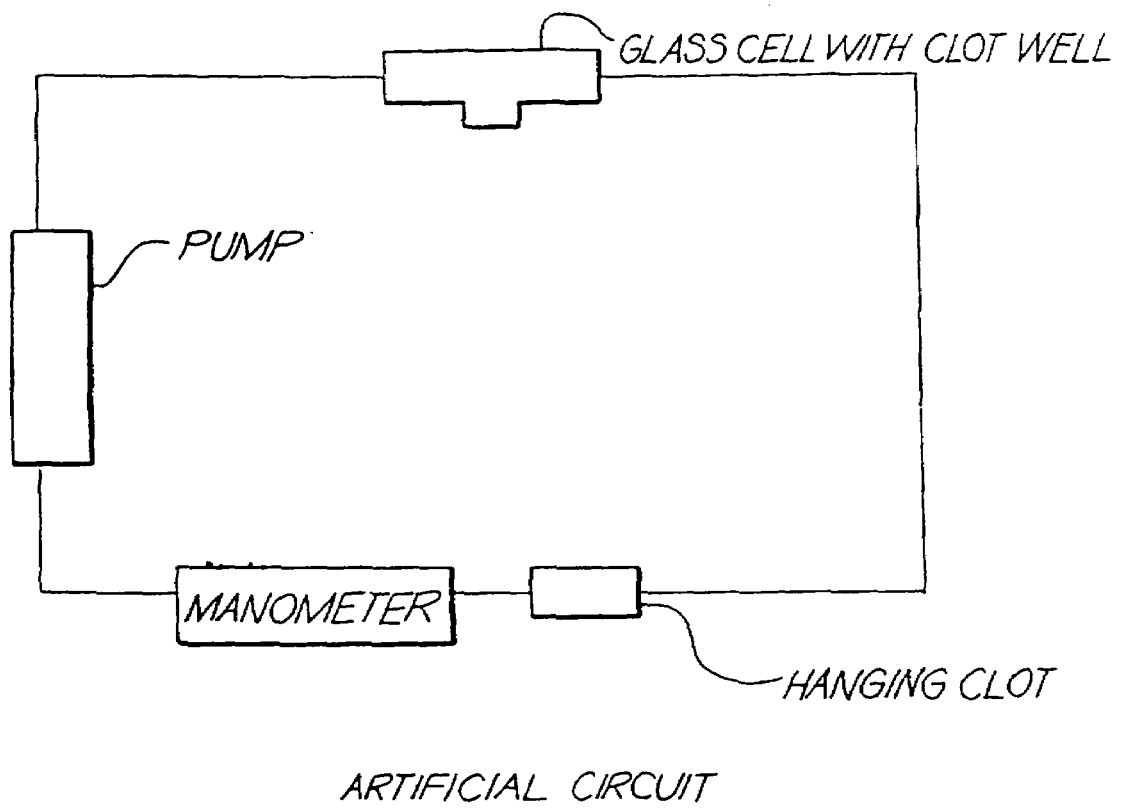
FIG. 2 is a schematic representation of the artificial circuit described in Example 13.

Study of the Binding of ThromboTrace to Fibrin in Dynamic Situation Using an Artificial Circuit Protocol: The artificial circuit is an adaptation of the chandler Loop attempting to simulate the vascular environment of the body. This experimental set-up allows the monitoring of the imaging of clots with the control of the parameters of flow and pressure. Fibrin network was developed from pooled human plasma obtained from healthy donors (by adding 1 U/mL bovine thrombin (Parke Davis) and 25 mMCaCl$_2$ (final concentration)) in a specially designed glass cell with a depressed well to house the clot. This design simulated an intramural clot with its surface exposed to the flowing medium. The clot was allowed to incubate at 37° C. for 30 min. The cell was connected with silicone tubing to the circuit comprised of a peristaltic pump and manometer (FIG. 2).

The circuit was filled with 50 mL normal saline containing 10% pooled human plasma and 1 mL TT (2 mCi/mL). The cell with clot was tilted so that the circulation mixture was not allowed to accumulate on top of the clot and was only trickling along the surface of the clot. A separate hanging clot was developed within a loop of copper wire and introduced into the circuit so that the total surface of the clot was exposed to the circulating media. Images were dynamically recorded using a gamma camera. Data acquisition time was 30 min. After that the circulation mixture was removed, the circuit was washed with normal saline and the image of the clot was acquired for another 10 minutes.

Figure 3:
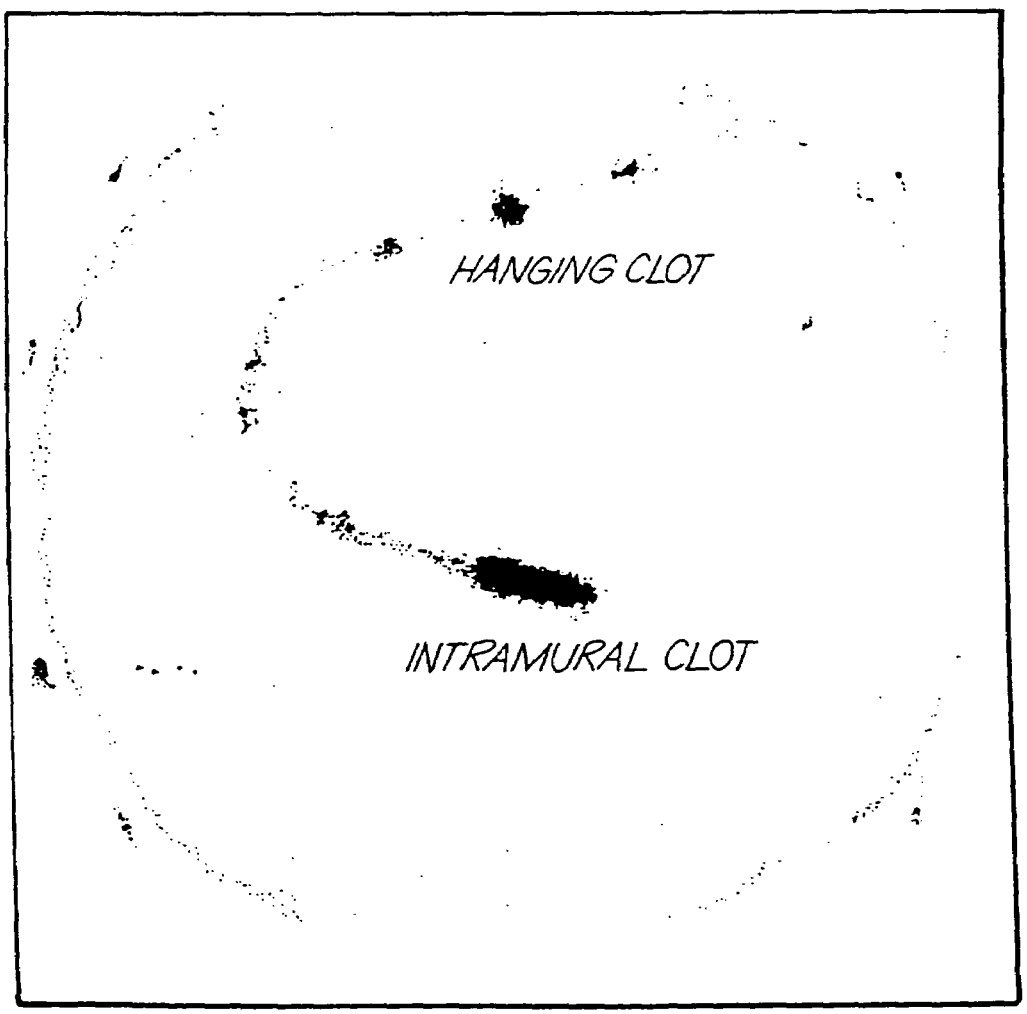
FIG. 3 shows the accumulation of radioactivity in the intramural clot in the artificial circuit of Example 13.

Results:

FIG. 3 shows the image of the clot after 30 min of dynamic labelling with ThromboTrace and after the silicone tubes and the clot were washed with normal saline. The bright spot in the circuit above the clot is that of the hanging clot formed within a small copper wire loop and simulating small clots found in the body.

Conclusion: It is obvious that both clots have been labelled with ThromboTrace and show up clearly.

EXAMPLE 14

Study of the Binding of ThomboTrace to Fibrin Using Transmission Electron Microscopy Protocol: Fibrin networks were developed from purified fibrinogen solution or plasma containing TT (by adding 1 U/mL bovine thrombin (Parke Davis) and 10mMCaCl$_2$ (final concentration)). They were primary fixed in 2.5% glutaraldehyde and postfixed in 2% osmium tetroxide. They were then stained en block with 2% uranyl acetate, washed in distilled water, dehydrated and embedded in Spurr resin. The samples were cut on a Reichert-Jung Ultracut. stained with Reinold's lead citrate stain and micrographs taken on Philips CM 10 TEM. Negative stained fibrin clots with TT were prepared on carbon grids preliminarily treated with glow discharge. The grids were washed in distilled water, dried and stained in 1% sodium phosphotungstate. They were then briefly washed and dried. Subsequently, micrographs were taken on a Philips 301 TEM.

Figure 4:
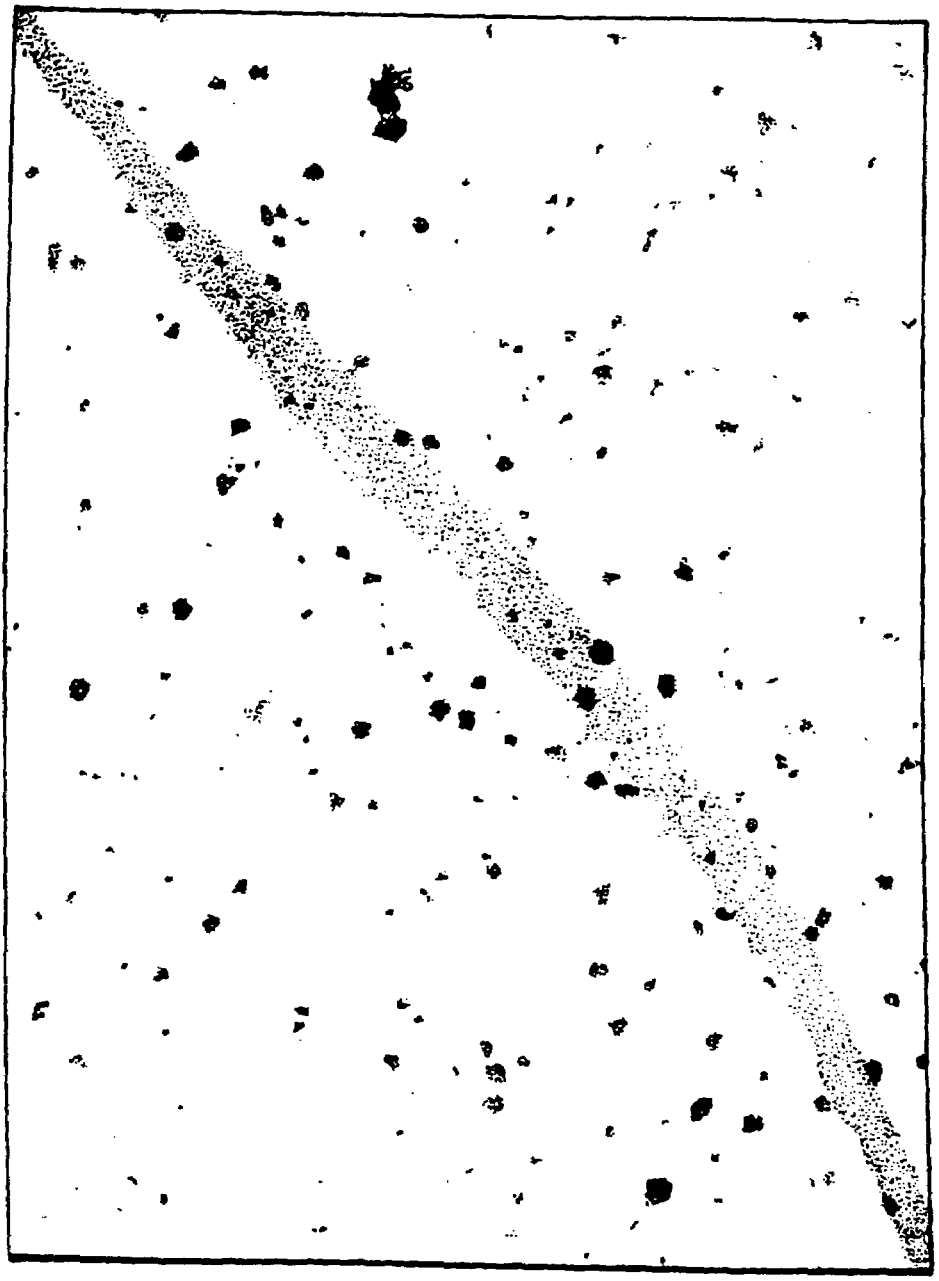
FIG. 4 shows the transmission electron micrography described in Example 14.

Results and Conclusions: FIG. 4 shows transmission electron micrography which reveals particles adhering to fibrin along fibres and specifically bound to dark bands of negatively stained fibrin thus denoting a specific binding site for particles.

EXAMPLE 15

Study of the Binding of ThromboTrace to Fibrin Monolayer Using Microwell Technique Protocol: 96 well PVC plates were coated with one of the following: PBS, solution of bovine serum albumin (BSA)/PBS. D-dimer, soluble fibrin, fibrin. The concentration of proteins directly coating well was 100 µg/mL. If proteins were raised from the surface by using 4D2/182 monoclonal antibody specific to fibrin(ogen) (AGEN) (10 µg/mL), the concentration of proteins was 100 µg/mL. Wells were washed 3 times with PBS/BSA buffer in between application of proteins or TT. Plates were incubated with TT at 37° C. for 30 min. Plates were washed with PBS/BSA buffer and each well was counted using a gamma-counter.

Results:

| Protein | % binding of TT compared to BSA-treated wells |
| --- | --- |
| Fibrinogen | 38 |
| Plasma + thrombin | 177 |
| D-dimer | 0 |
| Fibrin | 179 |
| Soluble Fibrin | 189 |

Conclusions: ThromboTrace binds with high affinity to fibrin monolayer and soluble fibrin. This affinity is not influenced by albumin or fibrinogen. In separate experiments it has been demonstrated that increasing the amount of fibrinogen does not inhibit the binding of TT to fibrin. ThromboTrace does not bind to D-dimer or albumin.

EXAMPLE 16

Study of the Effect of Surfactant ($C_{16}EO_6$) on the Binding of ThromboTrace to Fibrin Protocol: The studies have been performed using multi-well technique (Example 15). TT solution was prepared with different concentration of surfactant.

Results:

| Concentration of the surfactant (%) | % binding of TT compared to concentration of the surfactant |
|---|---|
| 0.0015 | 140 |
| 0.003 | 258 |
| 0.00625 | 194 |
| 0.0125 | 168 |
| 0.025 | 133 |
| 0.05 | 139 |

Conclusions: Binding is enhanced with $C_{16}EO_6$. Maximal binding is observed at the concentration of 0.003%.

The in vivo experiments described below were carried out on rabbits and a cat adhering to standard anaesthetising procedure according to the guidelines provided by the Australian National Health and Medical Research Council. All animals were injected with 1 ml. ThromboTrace (2 mCl/mL). Acquisition time for all images was 60 min.

EXAMPLE 17

Imaging of Clots in Rabbit Ear Vein

Figure 5:
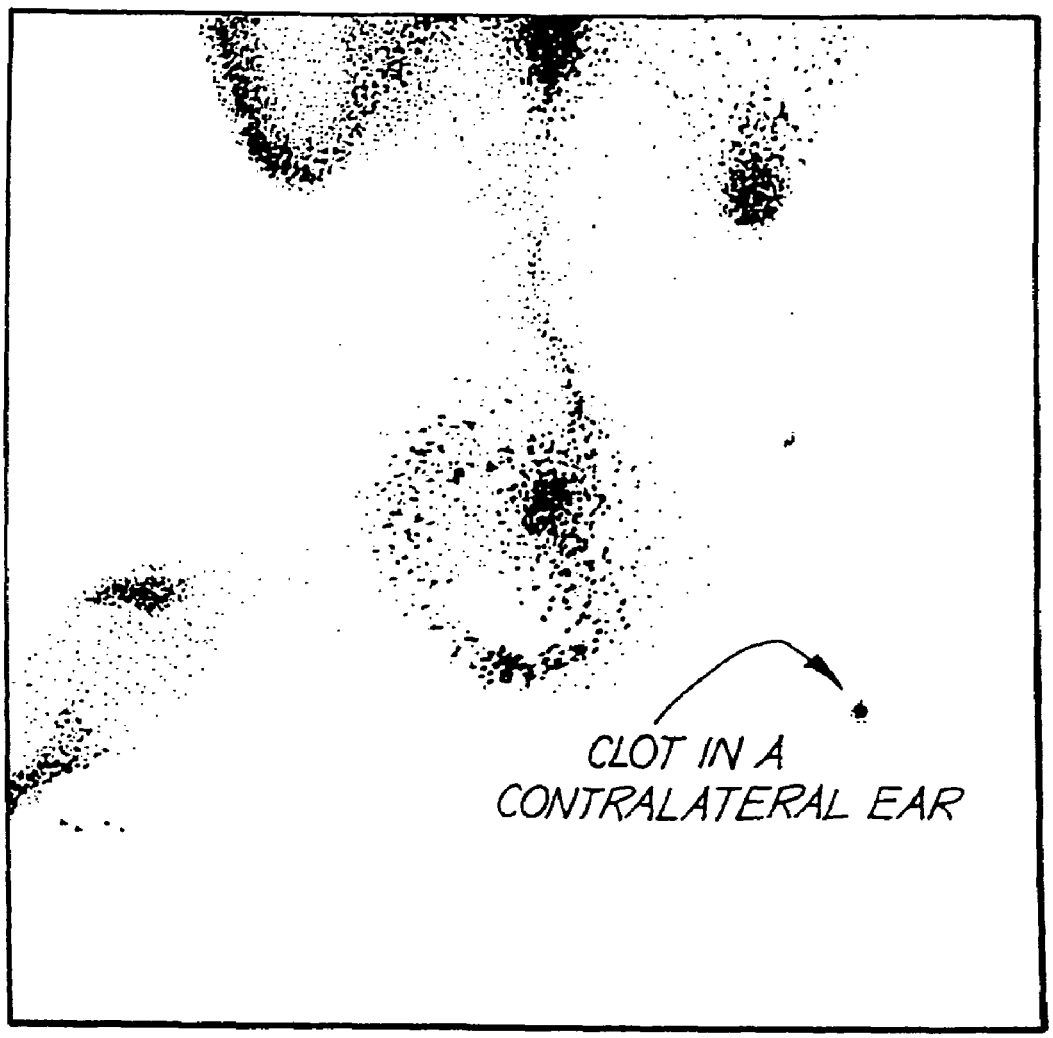
FIG. 5 shows imaging of clots in a rabbit ear vein described in Example 17.

Two needle stick injuries with 20 G needles were made in the right ear and one in the contralateral ear. ThromboTrace was injected into the ear vein of the right ear. As shown in FIG. 5 both right ear and contralateral ear injuries have been labelled with ThromboTrace.

EXAMPLE 18

Clot Caused by Intramuscular Injection of Anaesthetic

Figure 6:
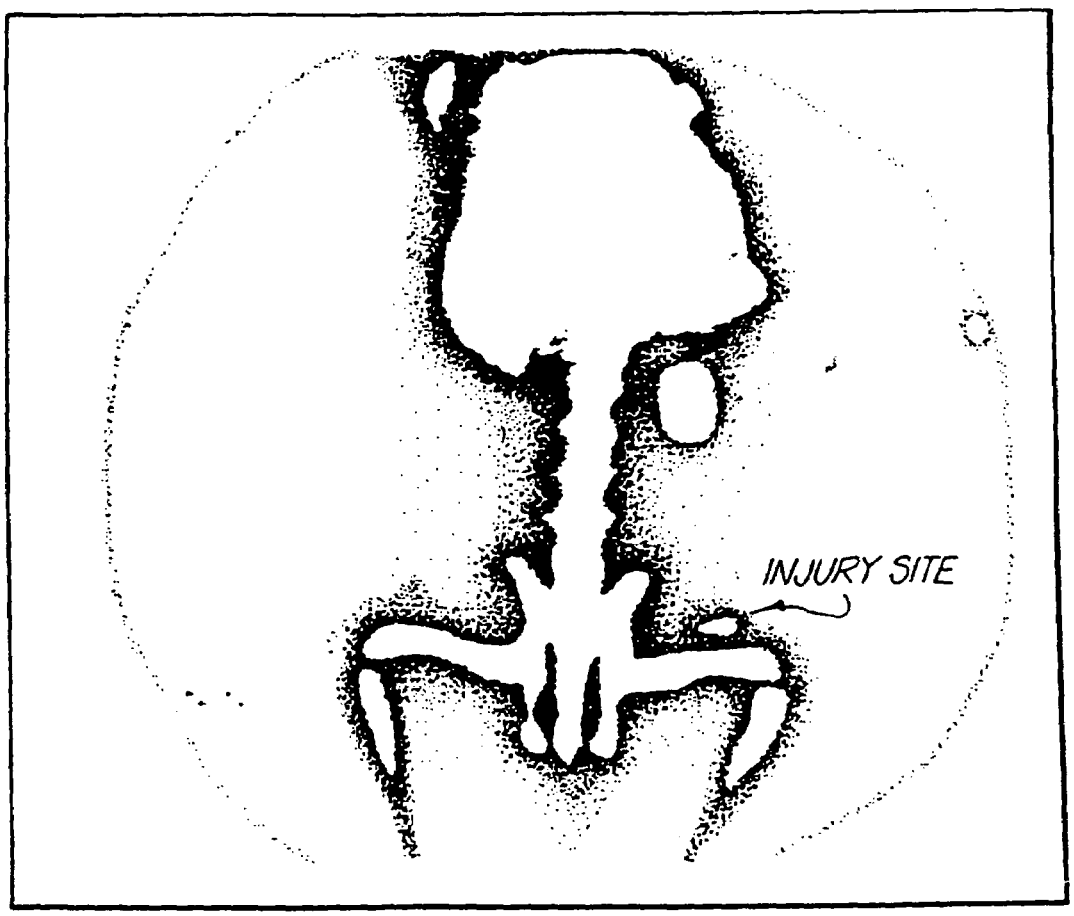
FIG. 6 shows a clot-caused by intramuscular injection of anaesthetic described in Example 18.

FIG. 6 shows a clot caused by intramuscular injection of anaesthetic in the left thigh. ThromboTrace was injected into the ear vein. This photograph is representative of imaging done both one hour after the injection and 24 hours post injury.

EXAMPLE 19

Imaging of Clot in Cat Femoral Vein

Figure 7:
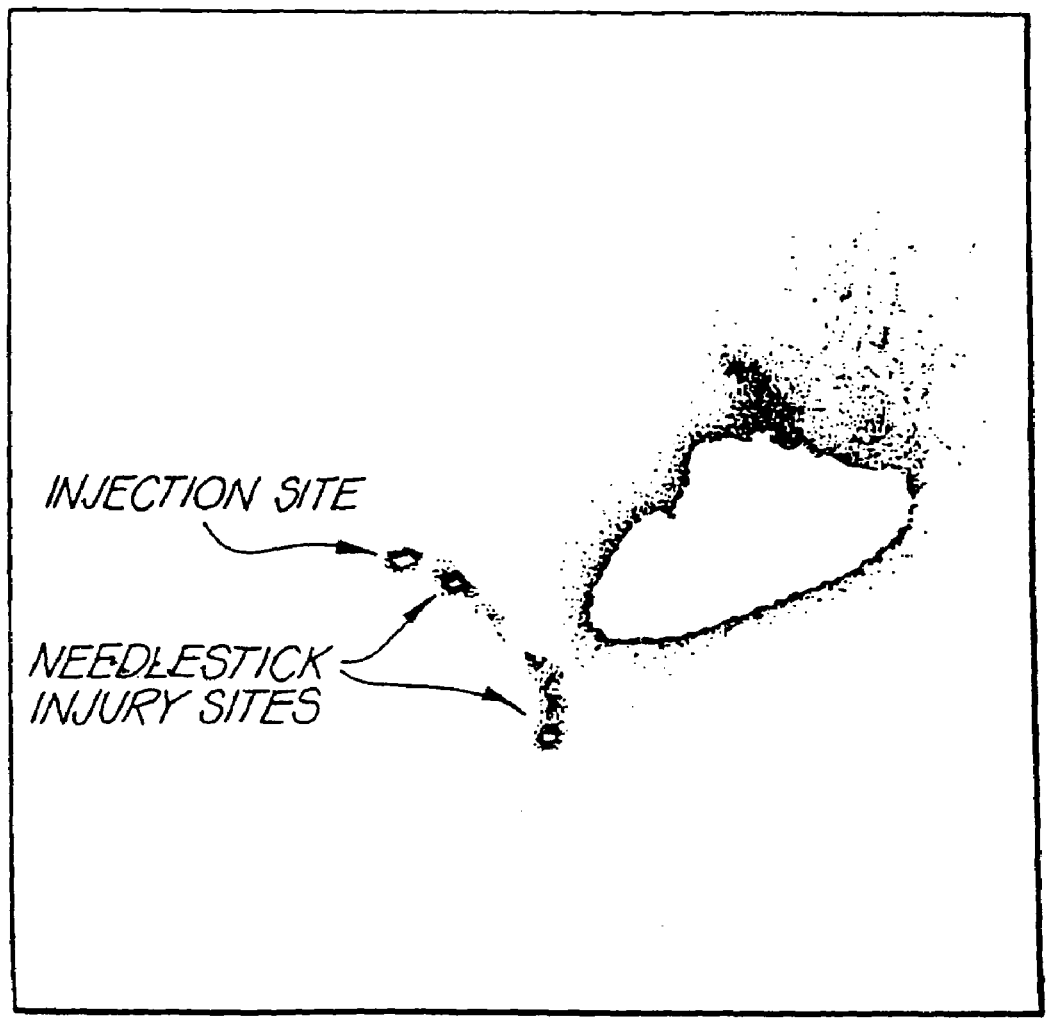
FIG. 7 shows the imaging of a clot in a cat femoral vein described in Example 19.

Needlestick injury was made in the femoral vein of a cat. ThromboTrace was introduced near the site of injury after one hours. The labelled clot is clearly visible in the FIG. 7. Further along the site of injury is a set of four bright spots. It is suspected that these were clots formed by previous injury to the animal. It was not possible to confirm this finding.

EXAMPLE 20

Imaging of Clot in Rabbit Pulmonary Vasculature

Figure 8:
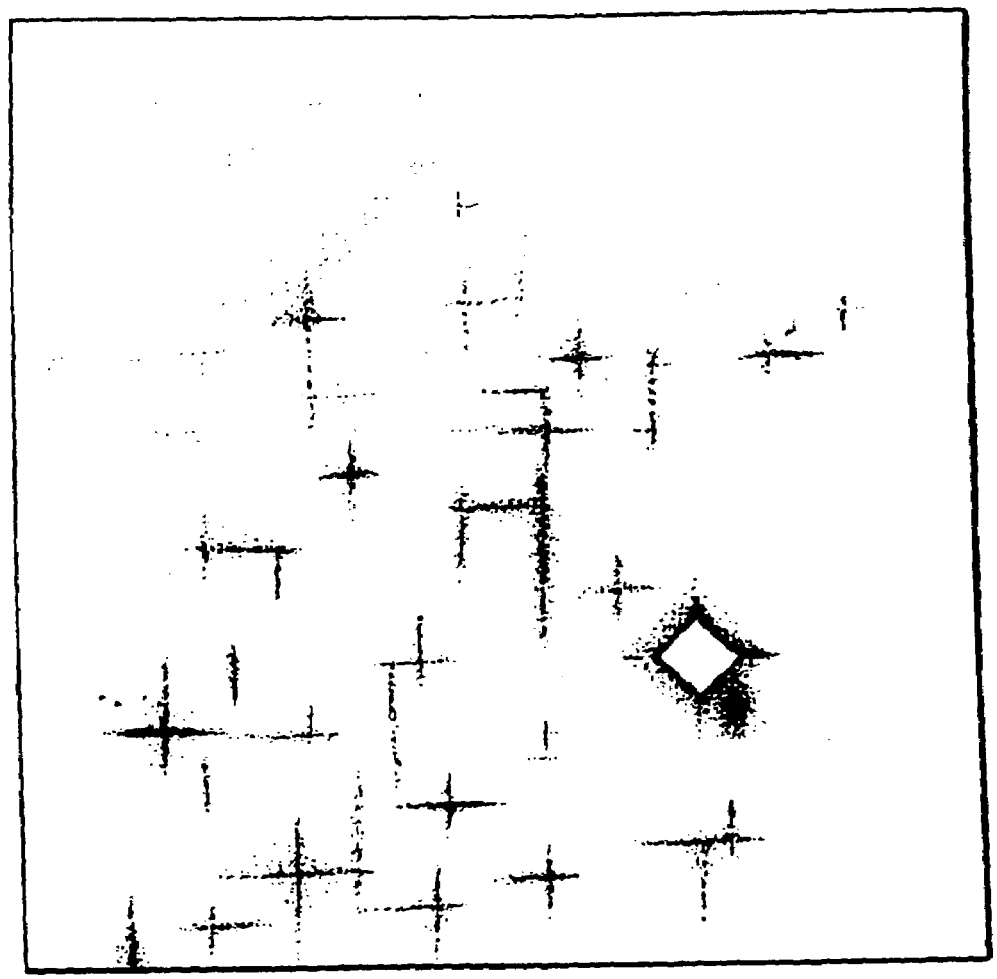
FIG. 8 shows the imaging of a clot in rabbit pulmonary vasculature described in Example 20.

Human blood clot was developed around a cotton thread in a polyurethane tube (diameter=3 mm) with 1 U/mL thrombin and 10 mMCaCl$_2$. After washing with normal saline a 1 mm length clot was introduced through a 16 or 18 G catheter into the jugular vein of a rabbit. After 10 min ThromboTrace was introduced through the catheter or through the central ear artery. The results are shown in FIG. 8. Classic wedging denoting depletion of vascular supply was seen in all cases.

EXAMPLE 21

Autoradiography of Rabbit Lungs with Pulmonary Emboli

Figure 9:
FIG. 9 shows the autoradiography of rabbit lungs with pulmonary emboli also described in Example 21.

Lungs were removed from the rib cage and autoradiographed to match images of clots obtained in vivo. The introduced human clot with cotton thread was then identified in the lung on post mortem and confirmed by two other witnesses and agreed that images obtained during the in vivo acquisition were in fact the introduced human blood clot The results are shown in FIG. 9.

EXAMPLE 22

Specificity of Particles for Equine Fibrin

In vitro experiments using plasma clots developed from equine blood also shows similar specificity of particles for equine fibrin. Studies utilised methods as described in Example 9. No significant difference was found between the binding characteristics of TT to horse fibrin and human fibrin.

EXAMPLE 23

Binding to Tumours

Figure 10:
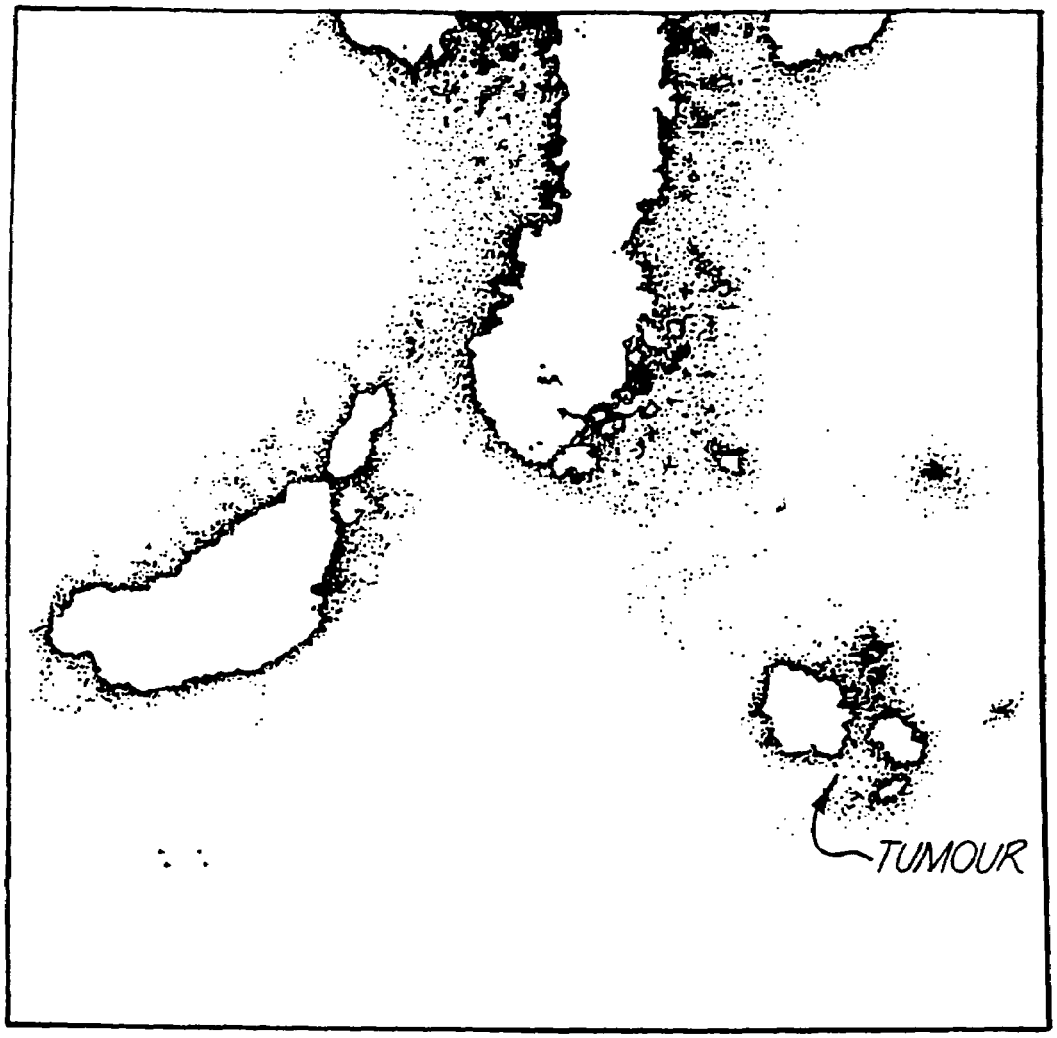
FIG. 10 shows the labelling of a small tumour in the ear of the rabbit as described in Example 23.
Figure 11:
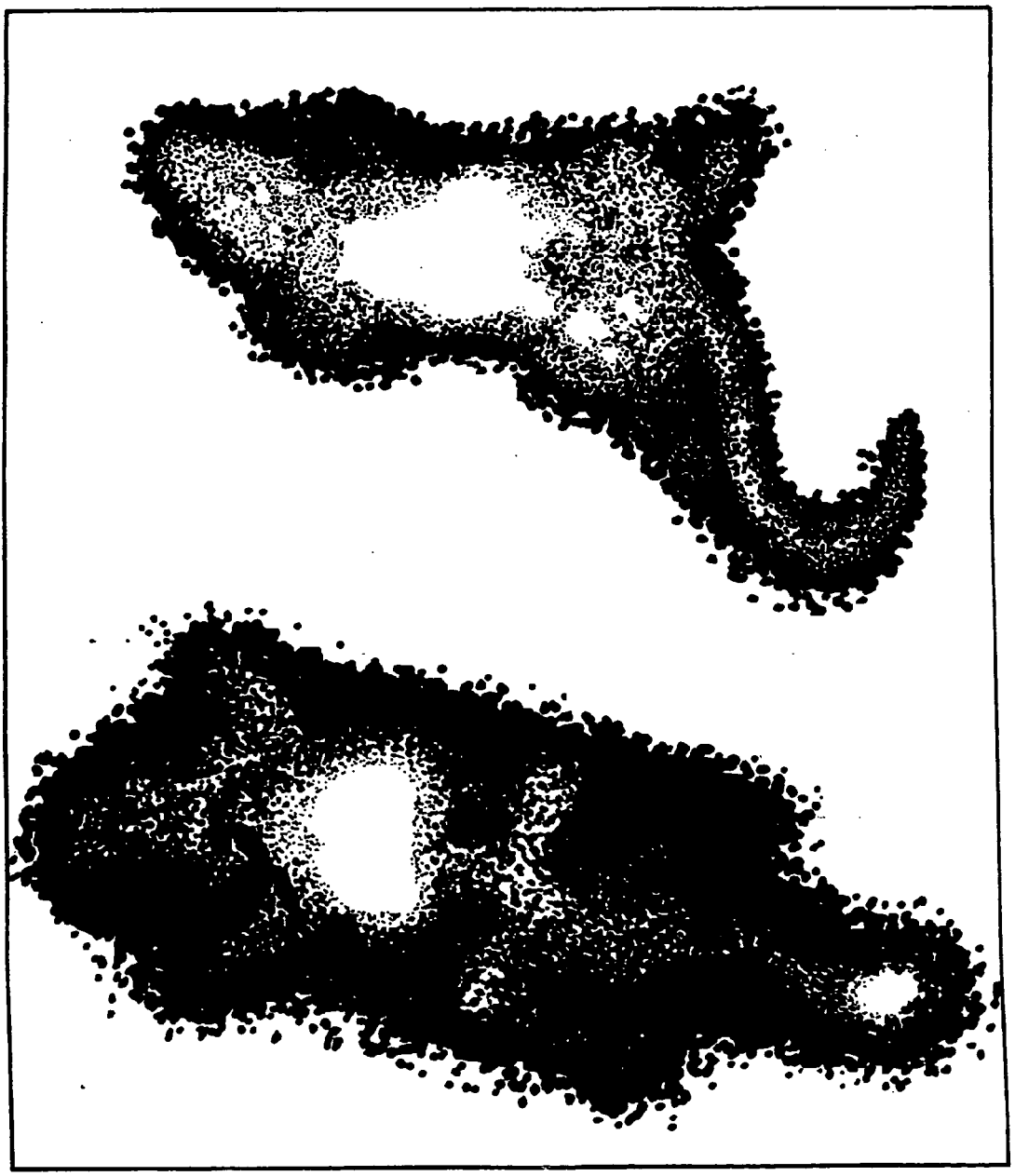
FIG. 11 shows the labelling of a mammary tumour in a Fischer strain rat as described in Example 23.
Figure 12:
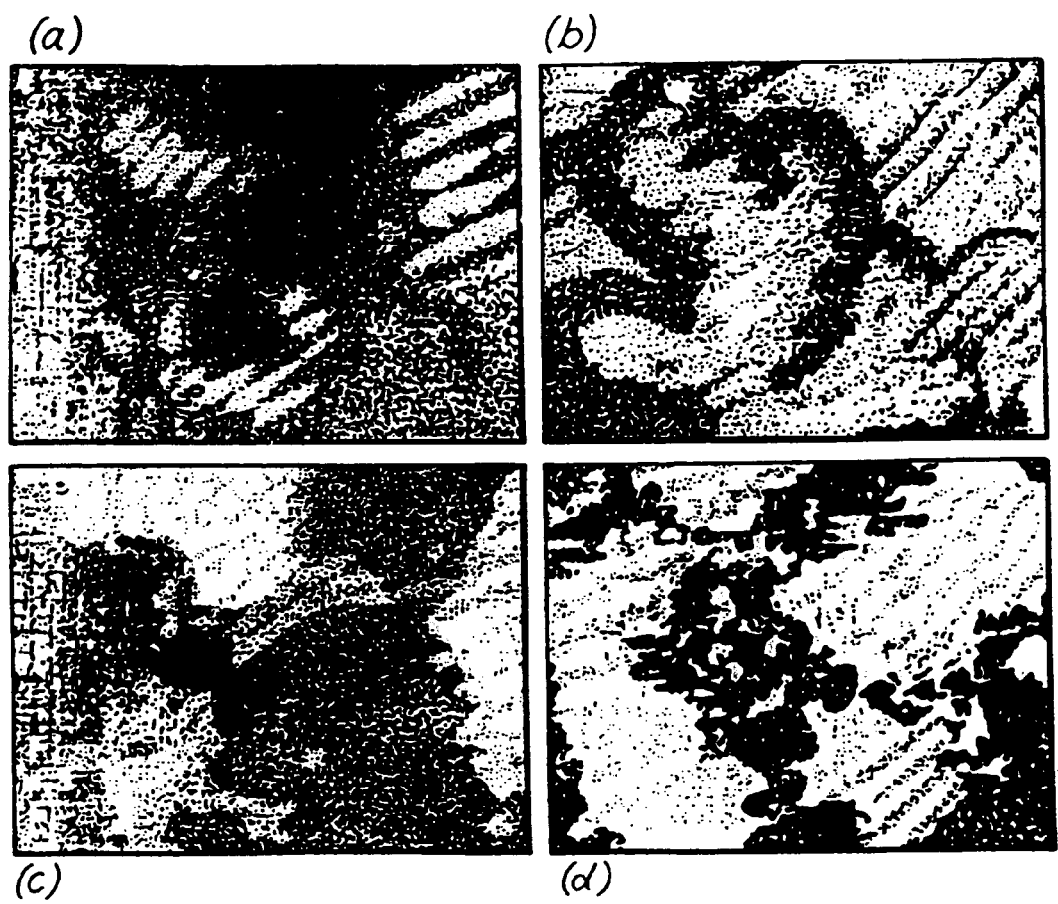
FIG. 12 shows particles with colloidal gold.

FIG. 10 shows the labelling of a small tumour on the ear of a rabbit. The experiment was performed as described in Example 7. Studies show that tumours on rabbit ear can be labelled using ThromboTrace, and the particles may thus be used in labelling tumours and cancers which have a fibrin sheath. Further conclusive evidence of this can be seen with reference to FIG. 11 which shows the labelling of a mammary tumour in a Fischer strain rat. In this case, cancer cells were injected subcutaneously and allowed to grow for a period of seven days. ThromboTrace was injected through the tail vein. The rat on the left of FIG. 11 is a control animal without cancer.

EXAMPLE 24

Bone Scan

Bone breakages are followed by a deposition of fibrin. In particular, hairline fractures are often difficult to distinguish and diagnose. The propensity of the particles to bind to fibrin provides another application as a label for bone fractures and therefore a frontline bone scan.

EXAMPLE 25

Binding to Soluble Fibrin

High affinity binding of ThromboTrace to soluble fibrin can be used as a basis for a diagnostic test for soluble fibrin which is reportedly a marker for cardiovascular disease and cancer among other diseases, e.g. Bredbacka et al. (1994 a & 1994 b), Ginsberg et al, (1995), Ginsberg et al, (1996), Iversen et al, (1995), Nakagawa et al, (1994), Shaukat et al, (1995). Experimental data set out in Example 15 demonstrates the binding of ThromboTrace to soluble fibrin.

EXAMPLE 26

Diagnostic Kit for Soluble Fibrin

Soluble fibrin bound particles are isolated and a suitable monoclonal antibody specific for soluble fibrin is attached to the soluble fibrin. An ELISA assay is then developed to specifically detect the quantity of the soluble fibrin in plasma.

Colloidal gold may be incorporated into these particles in order to strengthen the integrity of particles and increase the mass, thus increasing the sensitivity of the immunogold assay.

The affinity of the particles to soluble fibrin can then be used to detect the quantity of soluble fibrin again by utilising the immunogold type technique. Alternatively, it may be possible that the aggregation of particles caused when they bind to soluble fibrin may be used as the method of detection as these particles may exhibit a subtle colour change because of the aggregation or difference in light scattering.

EXAMPLE 27

Targeting Specific Drugs

A novel use for the particles is the coupling of anticoagulant drugs or clot specific drugs to the carbon shell. This can be established by the functionalisation of the carbon by amination or hydroxylation. These procedures will be accomplished using a radio frequency plasma field. Once functionalised these particles will then be coupled to drug molecules using commercially available kits. In fact one anticoagulant already available is biotinylated heparin which can then be coupled to the carbon shell.

Coupling to a drug is followed by Enzyme Immunoassay to ensure binding to fibrin is not disrupted These tests also show the effectiveness of these drugs when bound to the carbon. These coupled particles are then injected into an animal. The first injections are with radioactive technitium based particles which enables detection and further describes the kinetics of dissolution of the clots. If particles are coupled with tissue plasminogen activator for example, this indicates a rapid dissolution of the clot. If particles are heparin coupled these experiments will provide ample evidence that the heparin is in fact delivered to the site it is required. This is one major disadvantage of heparin usage at the moment.

INDUSTRIAL APPLICABILITY

It should be clear that the methods of detection of this invention will find wide use in the medical and veterinary fields.

The foregoing describes only some embodiments of the present invention and modifications obvious to those skilled in the art can be made thereto without departing from the scope of the invention.

REFERENCES

Bredbacka et al. Soluble fibrin: a predictor for the development and outcome of multiple organ failure. *Am J Hematol* 46:289–294, 1994 (a)

Bredbacka et al. Bredbacka et al. Soluble fibrin and D-dimer as detectors of hypercoagulability in patients with isolated brain trauma. *J Neurosurg Anesthesiol* 6:75–82, 1994 (b)

Ginsberg et al. Evaluation of a soluble fibrin assay in patients with suspected deep vein thrombosis. *Thromb Haemost* 75(3):833–836, 1995.

Ginsberg et al. Evaluation of a soluble fibrin assay in patients with suspected pulmonary embolism. *Thromb Haemost* 75(4):551–554, 1996

Iversen et al. Soluble fibrin in plasma before and after surgery for benign and malignant colorectal disease. *Thromb Res* 79:471–481, 1995

Nakagawa et al. Plasma levels of soluble fibrin in patients with malignancy-associated disseminated intravascular coagulation. *Blood Coagul Fibrinolysis* 5:725–730, 1994

Shaukat et al. Soluble fibrin: a marker of the development of thrombosis in coronary heart disease. *Thromb Haemost* 73(6):1141(922), 1995.

What is claimed is:

1. A method for the in vivo detection of fibrin, said method comprising the steps of:
   administering to said patient an effective amount of a detectable reagent comprising discrete diagnostic particles dispersed in a pharmaceutically or veterinarily acceptable carrier, diluent, excipient, adjuvant or any combination thereof, wherein said diagnostic particles comprise a detectable marker encased in at least two layers of carbon, wherein upon administration of said reagent said diagnostic particles are dispersed in the aqueous medium and form a stable colloid and wherein said particles are made by heating a carbon crucible having deposited thereon a detectable marker to a temperature in the range of 2250° C. to 3000° C. in an inert gas and in a sealed container, thereby generating particles suspended in said inert gas, and precipitating said particles suspended in said inert gas to form said diagnostic particles;
   binding said diagnostic particles to said fibrin, wherein said diagnostic particles exhibit a specific affinity for said fibrin; and
   detecting the presence of said detectable marker in said patient.

2. The method of claim 1 wherein said particles suspended in said inert gas are precipitated using an electrostatic precipitator.

3. The method according to claim 1, wherein the carrier is an aqueous solution.

4. The method according to claim 1, wherein the aqueous solution is 5% glucose in water.

5. The method according to claim 1, wherein a surface of said diagnostic particles is coated with a surfactant coating, thereby generating surfactant coated diagnostic particles, and wherein said surfactant coating increases the binding efficiency of said surfactant coated diagnostic particles with fibrin relative to diagnostic particles not having said surfactant coating.

6. The method of claim 1 wherein said diagnostic particles form a nanocolloid upon administration of said detectable reagent.

7. The method of claim 5, wherein said surfactant coating comprises $C_{16}EO_6$.

8. A method for the in vivo detection of fibrin present in the bloodstream of a subject, said method comprising the steps of:
   administering to the bloodstream of said subject an effective amount of a detectable reagent comprising discrete diagnostic particles dispersed in a pharmaceutically or veterinarily acceptable carrier, diluent, excipient, adjuvant or any combination thereof, wherein said diagnostic particles comprise a detectable marker encased in about 2 to 20 layers of carbon, wherein said diagnostic particles are made by heating a carbon crucible having deposited thereon a detectable marker to a temperature in the range of 2250° C. to 3000° C., thereby generating suspended particles, and precipitating said suspended particles to form said diagnostic particles, wherein upon administration of said reagent said diagnostic particles are dispersed in the aqueous medium and form a stable colloid;

binding said diagnostic particles to said fibrin, wherein said diagnostic particles exhibit a specific affinity for said fibrin; and detecting the presence of said detectable marker in said bloodstream of said subject.

9. A method for the in vivo detection of fibrin present in a blood vessel of a subject, said method comprising the steps of:

administering into said blood vessel of the subject an effective amount of a detectable reagent comprising discrete diagnostic particles dispersed in a pharmaceutically or veterinarily acceptable carrier, diluent, excipient, adjuvant or any combination thereof, wherein said diagnostic particles comprise a detectable marker encased in at least two layers of carbon, wherein said diagnostic particles are made by heating a carbon crucible having deposited thereon a detectable marker to a temperature in the range of 2250° C. to 3000° C., thereby generating suspended particles, and precipitating said suspended particles to form said diagnostic particles, wherein upon administration of said reagent said diagnostic particles are dispersed in the aqueous medium and form a stable colloid;

binding said diagnostic particles to said fibrin, wherein said diagnostic particles exhibit a specific affinity for said fibrin; and detecting the presence of said detectable marker in said blood vessel of said subject.

* * * * *